(12) United States Patent
Benkert et al.

(10) Patent No.: US 10,197,542 B2
(45) Date of Patent: Feb. 5, 2019

(54) MEASURING ARRANGEMENT

(71) Applicant: Endress + Hauser Conducta Gesellschaft für Mess—und Regeltechnik mbH + Co. KG, Gerlingen (DE)

(72) Inventors: Tilman Benkert, Stuttgart (DE); Bjorn Haase, Stuttgart (DE); Gunter Jahl, Lochgau (DE); Stefan Robl, Hunxe (DE)

(73) Assignee: Endress+Hauser Conducta GmbH+Co. KG, Gerlingen (DE)

( * ) Notice: Subject to any disclaimer, the term of this patent is extended or adjusted under 35 U.S.C. 154(b) by 1190 days.

(21) Appl. No.: 14/323,093

(22) Filed: Jul. 3, 2014

(65) Prior Publication Data

US 2015/0007636 A1 Jan. 8, 2015

(30) Foreign Application Priority Data

Jul. 3, 2013 (DE) .................. 10 2013 106 977
Jul. 25, 2013 (DE) .................. 10 2013 107 964

(51) Int. Cl.
*G01N 33/00* (2006.01)

(52) U.S. Cl.
CPC ......... *G01N 33/0009* (2013.01); *G01N 33/00* (2013.01); *G01N 33/0073* (2013.01)

(58) Field of Classification Search
CPC ............ G01N 33/00; G01N 33/0009; G01N 33/0073; G01F 15/061; G01F 15/022; G05B 19/0426
See application file for complete search history.

(56) References Cited

U.S. PATENT DOCUMENTS 7,886,614 B2 * 2/2011 Koudal ................. G01F 1/8431
                                                         73/861.08
8,762,598 B2    6/2014 Wittmer
(Continued)

FOREIGN PATENT DOCUMENTS

CN      201782756 U    4/2011
CN      202758213 U    2/2013
(Continued)

OTHER PUBLICATIONS

German Search Report, German PTO, Munich, dated Dec. 19, 2013.
(Continued)

*Primary Examiner* — Mohamed Barakat
(74) *Attorney, Agent, or Firm* — Mark A. Logan; PatServe

(57) ABSTRACT

A measuring arrangement, which includes: a sensor, wherein the sensor is embodied to produce a measurement signal correlated with a measured variable, a first interface, an evaluation circuit least one computer system and a memory associated with the computer system, as well as a third interface, especially a third interface embodied as a fieldbus interface, a first superordinated data processing system, with which the evaluation circuit is connected via the third interface, wherein in the memory associated with the computer system of the evaluation circuit a computer program executable by the computer system is stored, wherein the computer program serves for additional processing of the measurement signal as well as serving for transmission of the further processed measurement signal via the third interface to the first superordinated data processing system; and a second superordinated data processing system connected wirelessly, especially via a radio connection, with the evaluation circuit.

19 Claims, 3 Drawing Sheets

(56) References Cited

U.S. PATENT DOCUMENTS

| | | | | |
|---|---|---|---|---|
| 2003/0183001 A1* | 10/2003 | Zimmermann | ....... | G01F 15/022 |
| | | | | 73/295 |
| 2011/0153040 A1 | 6/2011 | Wittmer | | |
| 2011/0208440 A1* | 8/2011 | Pechstein | ............... | G01D 21/00 |
| | | | | 702/30 |
| 2013/0046501 A1* | 2/2013 | Nentwich | .............. | G05B 21/02 |
| | | | | 702/104 |

FOREIGN PATENT DOCUMENTS

| | | | | |
|---|---|---|---|---|
| DE | 102009055247 A1 | | 6/2011 | |
| DE | 102011104295 A1 * | 12/2012 | .......... | B25J 19/0079 |
| EP | 2233994 A2 * | 9/2010 | ........... | G05B 19/042 |

OTHER PUBLICATIONS

Qian Zhiwei,"Design and Implementation of the Wireless Teletransmission Pressure Monitoring System", Chinese Masters Theses Full-text Database—Information Science and Technology, Jun. 15, 2013, pp. I136-I517, vol. 6, 2013, China Academic Journal Electronic Periodical House (CAJEPH), China (English Translation Provided).

* cited by examiner

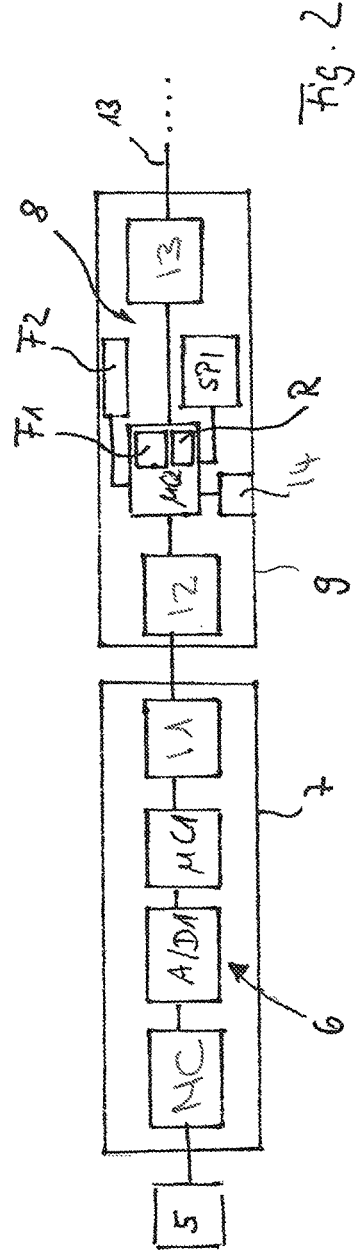
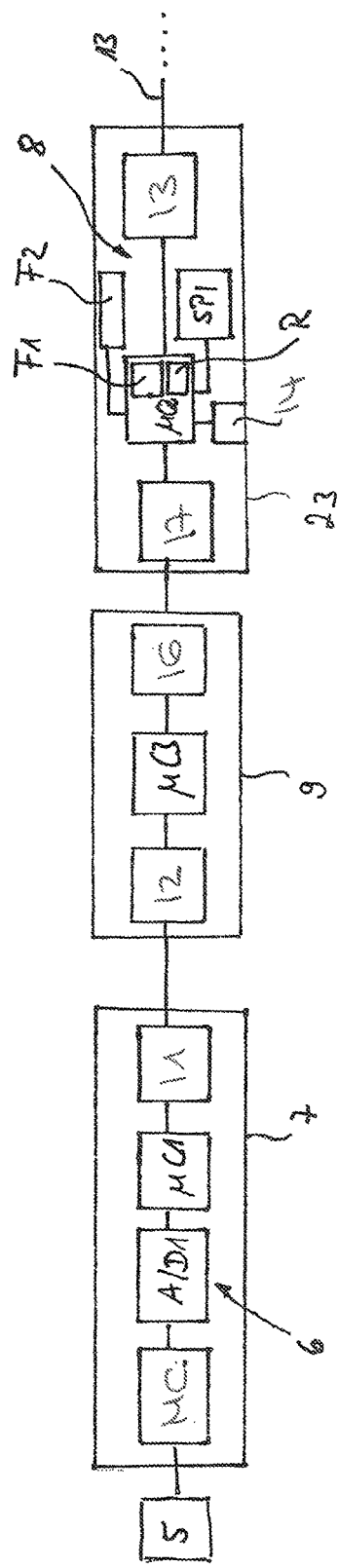

MEASURING ARRANGEMENT

TECHNICAL FIELD

The invention relates to a measuring arrangement, especially a measuring arrangement for process measurements technology.

BACKGROUND DISCUSSION

So-called field devices, i.e. measuring devices installed near to a process, are applied in process measurements technology, especially for automation of chemical processes and/or for automation of procedures for producing a product from a raw or starting material by the use of chemical, physical or biological processes and/or for control of industrial plants. Field devices embodied as sensors can monitor, for example, process measurement variables such as pressure, temperature, flow, fill level or measurement variables of liquid and/or gas analysis, such as, for example, pH-value, conductivity, concentrations of certain ions, chemical compounds and/or concentrations or partial pressures of gases.

Frequently, a large number of most varied sensors are used in a process installation. A sensor arranged at a certain location of installation in the process, for example, a sensor installed at a certain location and embodied for registering one or more measurement variables, forms a measuring point.

A sensor includes, as a rule, a measuring transducer, which is embodied to register the measured variable to be monitored and to produce an electrical measurement signal correlated with the current value of the measured variable. Serving today for additional processing of the measurement signal is most often an electronic, evaluation circuit, which is embodied to condition the electrical, measurement signal further, for example, to digitize it, to convert it into a measured value of the measured variable and/or into a variable derived from the measured value, and, in given cases, to output such to a superordinated unit. The evaluation circuit can perform, besides measured value formation and measured value forwarding, more extensive functions. For example, it can be embodied to perform a more extensive evaluation of the measured values or to conduct sensor diagnostics, in the case of which a current state of the sensor is determined and/or a prediction of the remaining life of the sensor occurs.

In the case of sensors of the aforementioned type, the evaluation circuit is frequently connected with a superordinated data processing system most often arranged spatially removed from the respective measuring point. Measured values produced by the respective sensor, diagnosis relevant data or other sensor data are forwarded to the superordinated data processing system. The superordinated data processing system can especially include one or more electronic process controllers, for example, one or more on-site, measurement transmitters, a process control computer or a programmable logic controller (PLC).

Frequently serving, at least sectionally, for data transmission in such industrial measuring arrangements are fieldbus systems, such as, for example, FOUNDATION Fieldbus, PROFIBUS, ModBus, etc. or, for example, also networks based on the Ethernet standard. Accompanying these fieldbus systems are the corresponding, most often application independently standardized, transmission protocols.

Known from published International Application WO 2005/031339 is a liquid sensor, which is connected via a coupling with a measurement transmitter and further with a superordinated data processing system. The sensor includes a measuring transducer and a sensor circuit, which has a preprocessing circuit for preprocessing the analog measuring signals produced by means of the measuring transducer, an analog/digital converter for converting the registered, analog, measurement signals into digital measurement signals and a first interface for transmitting the digital measurement signals to the superordinated measurement transmitter. The coupling comprises a sensor side, primary coupling element and a complementary, secondary coupling element, which is connected with the measurement transmitter. The first interface is embodied to transmit the digital measurement signals via the coupling to the measurement transmitter. The secondary coupling element includes another electronic circuit, which has, complementary to the first interface, a second interface, which is embodied to receive the measurement signals transmitted from the first interface. The second interface can, moreover, transmit data as well as energy via the coupling to the first interface of the sensor. The transmission of energy and data occurs in the case of the sensor known from published International Application WO 2005/031339 A1 contactlessly by means of an inductive coupling of the first and second interfaces. This assures also a galvanic decoupling of the sensor from the measurement transmitter.

Measurement transmitters conventionally have display means, e.g. a display, and input means, e.g. in the form of a keyboard or one or more rotate/press switches, by means of which a user can read measured values and sensor data, respectively input parameters or commands.

In earlier times, measuring arrangements existed, which did without a conventional measurement transmitter having input and display means. Described in German Patent DE 10 2011 107 717 A1 is a sensor for liquid or/and gas analysis, which is connected with a measuring or/and evaluation circuit, respectively with a superordinated control system. The sensor includes a sensor housing, in which are provided circuit means for registering, conditioning and forwarding measured values to the measuring- or/and evaluation circuit, respectively to the control system. This circuit means comprises an analog sensor electronics, an analog/digital converter for converting the registered analog, measured values into digital, measured values, a computing unit and communication means for conditioning and forwarding the digital measured values to the measuring or/and evaluation circuit, respectively to the control system, using a standard communication protocol of process technology, for example, HART, PROFIBUS PA, PROFIBUS DB or Foundation Fieldbus. Goal of the sensor construction illustrated in German Patent DE 102011107717 A1 is to integrate as much electronics as possible into the sensor. Thus the sensor electronics arranged in the sensor housing is embodied not only for registering and, in given cases, digitizing the measured values registered by a measuring transducer of the sensor but also for additional processing and conversion of the measured values into a standard communication protocol processable by the control station.

Sensors for liquid and/or gas analysis must, during their lifetime, as a rule, from time to time, undergo maintenance, especially be calibrated or regenerated. To this end, frequently the sensor to be maintained is removed from the measuring point and the maintenance measure performed at another location, for example, in the laboratory. In the intervening time, the measuring point can be operated further with another sensor of the same type. The lifetime of sensors for liquid and/or gas analysis is, moreover, limited and depends on the particular features of the measuring point. Lifetime can lie, for example, between a few days and some months. This leads to the fact that the sensors of a measuring point must regularly be replaced. A disadvantage of a measuring arrangement, in the case of which as much electronics as possible is accommodated in the sensor, is, thus, that, in the case of each sensor replacement, not only data stored in the sensor, but, instead, also measuring point specifically matched parameters and measuring location specific program code get removed from the measuring point. These parameters, respectively program code, must be provided anew to the replacement sensor. Moreover, the lifetime of the components of a sensor electronics is clearly longer than the usual lifetime of the measuring transducer of the sensor. It is, consequently, uneconomic to replace these components with the same frequency as the measuring transducer.

European Patent EP 2 233 994 A2 describes a measuring arrangement, which includes an intelligent, process sensor, which is connectable releasably with an electronics module. The electronics module includes a microprocessor with a memory unit, a plurality of digital interfaces and a means for forwarding analog signals from the process sensor to a process control system. The process sensor serves for determining at least one chemical or physical, measured variable of a measured medium and includes, besides a measuring transducer for registering the measured variable, an electronics unit connected inseparably with the measuring transducer. The electronics unit comprises a means for monitoring the sensor state, a means for digitizing the analog measurement data from the sensor unit, a means for forwarding the analog and digitized data, at least one analog interface and at least one digital interface for connection of the process sensor with the process control system, and a galvanic isolation between the measured medium and the interfaces. The electronics unit connected inseparably with the measuring transducer serves to process measurement data, to monitor the sensor state and to store the sensor relevant data. In general, it performs, thus, functions of an otherwise usual measurement transmitter in the field of analytical measurements technology. The electronics module serves to output the data and diagnostic information provided by the intelligent sensor via one or more interfaces, for example, to a process control system or to a mobile servicing device using a communication protocol processable by the process control system, respectively by the mobile servicing device. Since also here essential measurement transmitter functionalities are provided by an electronics inseparably connected with the measuring transducer, the measuring arrangement known from European Patent EP 2 233 994 A2 has essentially the same disadvantages as the apparatus described in German Patent DE 10 2011 107 717 A1.

SUMMARY OF THE INVENTION

It is, therefore, an object of the present invention to provide a measuring arrangement, which overcomes, at least partially, the described disadvantages of the state of the art.

This object is achieved by a measuring arrangement, comprising: a sensor, especially a sensor for liquid and/or gas analysis, wherein the sensor is embodied to produce a measurement signal correlated with a measured variable and to output such measurement signal via a first interface; an evaluation circuit connected with the sensor via a second interface complementary with the first interface and connected releasably with the first interface, wherein the evaluation circuit includes at least one computer system and a memory associated with the computer system, as well as a third interface, especially a third interface embodied as a fieldbus interface; a first superordinated data processing system, especially one embodied as a superordinated control system, with which the evaluation circuit is connected via the third interface, wherein in the memory associated with the computer system of the evaluation circuit a computer program executable by the computer system is stored, wherein the computer program serves for additional processing of the measurement signal, as well as serving for transmission of the further processed measurement signal via the third interface to the first superordinated data processing system; and a second superordinated data processing system connected wirelessly, especially via a radio connection, with the evaluation circuit.

The measuring arrangement of the invention includes:
- a sensor, especially a sensor for liquid and/or gas analysis, wherein the sensor is embodied to produce a measurement signal correlated with a measured variable and to output such measurement signal via a first interface,
- an evaluation circuit connected with the sensor via a second interface complementary to the first interface and connected releasably with the first interface, wherein the evaluation circuit includes at least one computer system and a memory associated with the computer system, as well as a third interface, especially a third interface embodied as a fieldbus interface,
- a first superordinated data processing system, especially one embodied as a superordinated control system, with which the evaluation circuit is connected via the third interface, wherein in the memory associated with the computer system of the evaluation circuit a computer program executable by the computer system is stored, wherein the computer program serves for additional processing of the measurement signal, especially the calculating of a measured value based on the measurement signal, as well as serving for transmission of the further processed measurement signal via the second interface to the first superordinated data processing system; and
- a second superordinated data processing system connected wirelessly, especially via a radio connection, with the evaluation circuit.

The evaluation circuit can be embodied, for example, to process further a measurement signal delivered by the sensor, especially, based on the measurement signal, to determine a measured value of the measured variable to be monitored by the measuring arrangement, to convert the calculated measured value into a signal according to a communication protocol processable by the first and/or second data processing system and to forward such to these. The evaluation circuit can be embodied, moreover, to monitor the state of the sensor, respectively a current state of the sensor, for example, to ascertain a remaining life or a current counter reading, as well as to store sensor, or measuring point, referenced data and parameters, wherein one or more computer programs serving the mentioned purposes are stored in a memory of the evaluation circuit. The computer system can be, for example, a microprocessor.

In an embodiment, the sensor and the evaluation circuit are connected with one another by means of a releasable, plugged connection for transmission of data and energy, wherein the plugged connection includes a sensor side, primary coupling element and a thereto complementary, evaluation circuit side, secondary coupling element, wherein the secondary coupling element has a housing, in which the evaluation circuit is arranged. The coupling elements can especially be a plug, respectively a socket, of a plugged connection.

Since the evaluation circuit serving for further processing of the sensor signal is connected separably with the sensor, e.g. in that it is integrated in a coupling element of the releasable plugged connection, which can be connected releasably with a complementary coupling element permanently connected with the sensor on the sensor side, an option is provided that the sensor can be replaced with a same type sensor, without losing the data and computer programs provided to the sensor connected earlier at the measuring point or without requiring additional measures, in order to provide these data or computer programs to the new sensor. Moreover, a sensor circuit connected permanently with the sensor for generating and for outputting the measurement signal, especially an electronic sensor circuit, can be constructed relatively simply, so that the sensor circuit simultaneously to be disposed of upon reaching the end of life of the sensor can be embodied of few and/or price favorable components. Since the evaluating electronics is accommodated in a housing of the coupling element, the measuring arrangement is, as a whole, compact.

Because the evaluation circuit is embodied for communication with the first and/or second data processing system, a servicing of the sensor or the measuring point, especially the retrieving of measured values or of sensor specific or measuring location specific, data or parameters stored in a memory of the evaluation circuit, as well as the inputting of configuration parameters or of commands can occur selectively by means of the first or by means of the second data processing system. For this, the first and/or the second data processing system can have corresponding display and input means, especially an HMI (Human Machine Interface). In this way, an option is provided for omitting a measurement transmitter installed permanently at the measuring point and having its own display/input means.

The housing of the secondary coupling element can in an advantageous embodiment of the evaluation circuit protect the evaluation circuit from environmental influences, especially by liquid tight or water spray tight sealing. The housing of the secondary coupling element can be embodied, for example, in one piece as a plastic injection molded part connected on one end sealedly, especially hermetically, with a cable, which contacts the evaluation circuit arranged in the interior of the housing and connects such with the superordinated first data processing system.

The housing of the secondary coupling element can be embodied at least sectionally as a hollow cylinder with an outer diameter of less than 20 mm. Especially, the outer diameter of the hollow cylinder can be greater than 10 mm. The sensor-side coupling element can correspondingly likewise be embodied at least sectionally as a hollow cylinder with an outer diameter of less than 20 mm, wherein the outer diameter is, however, greater than 10 mm. Preferably, the outer diameter of the coupling element measured perpendicularly to a sensor axis, respectively to a rotational symmetry axis of the coupling element, is at no position greater than 20 mm. This means that the sensor as well as the plugged connection can fit in a standard retractable assembly of process technology.

Advantageously, moreover, the evaluation circuit is arranged at least partially on a multi-ply circuit card, a multilayer circuit board or a flexible circuit board, respectively a rigid-flex circuit board. In this way, a yet more compact embodiment of the plugged connection, especially of the secondary coupling element, can be embodied.

The secondary and/or the primary coupling element can have a display element, which can comprise especially at least one LED (Light Emitting Diode) for displaying a communication state or a system state, especially a state of the sensor. The display element can comprise, for example, different colored LEDs, wherein different colors display different communication states. If only one individual LED is used, the displaying of various communication states can be shown by different blink rhythms.

The second superordinated data processing system can be embodied to communicate via a radio connection with the evaluation circuit according to a Bluetooth standard, especially in an energy-saving mode (HOLD, SNIFF, PARK) or according to the Bluetooth low energy protocol. For this, the evaluation circuit can include a radio transceiver, preferably a radio transceiver likewise arranged within the housing of the secondary coupling element.

The fieldbus interface of the evaluation circuit can be embodied to transmit data, especially further processed measured values, from the evaluation circuit to the first superordinated data processing system via a fieldbus in the form of a signal according to a protocol meeting one of the following standards: HART, PROFIBUS PA, PROFIBUS DB, Foundation Fieldbus, ModBus. Correspondingly, the fieldbus interface can be embodied to receive data from the first superordinated data processing system via the fieldbus in the form of a signal according to a protocol meeting one of the mentioned standards. The fieldbus interface can especially be embodied to enable communication of the evaluation circuit with the superordinated unit via a 4 to 20 mA HART signal.

The second superordinated data processing system can especially be mobile. For example, the second data processing system can be a handheld, such as, for example, the handheld sold by the Endress+Hauser group of firms under the mark, Field Xpert, a smart phone, a tablet PC, a notebook, or some other portable minicomputer.

The second data processing system can also be a display system. The display system can be, for example, a display embodied for wireless communication with the evaluation circuit and/or with the first superordinated data processing system.

The second data processing system can also be a handheld adapted for use in an Ex-region or a display system adapted for use in an Ex-region and embodied for wireless communication with the evaluation circuit.

The second superordinated data processing system can serve especially for servicing the sensor on-site, i.e. in the field. To this end, the evaluation circuit is embodied to transmit the measured value, current configuration parameters, which can be selected to be sensor or measuring point related, and menu structure data to the second data processing system. Conversely, the second superordinated data processing system can be embodied to transmit user predetermined, sensor or measuring-point specific, configuration parameters to the evaluation circuit. The second data processing system can comprise a computer program, especially a so-called app, which provides an HMI functionality. The terminology, HMI functionality, means, especially, that the app is embodied to represent on a display of the data processing system a menu structure, by means of which a user can look at measurement data or other data provided by the evaluation circuit, respectively input configuration parameters or commands by means of an input via input means of the second data processing system, for example, a touch display or a keyboard. In currently usual operating systems of smartphones, mobile minicomputers or tablet- PCs, such programs are either preinstalled or can be easily acquired, for example, via a central store of the smart phone or sensor manufacturer.

The second data processing system can supplementally have a communication interface to a radio network, such as WLAN, GSM or UMTS. This permits a connection of the second data processing system to a company-wide intranet of the operator of the measuring arrangement or of the sensor manufacturer or even a connection to the Internet. Via this communication interface, the second data processing system can download additional information concerning the sensor or additional computer program packages.

The computer program, which is executable by the computer system and which is stored in a memory associated with the computer system of the evaluation circuit, is, in a preferred embodiment, constructed modularly. The computer program includes, in such case, a general module, which is embodied to detect the sensor type of the sensor connected with the evaluation circuit. This can occur, for example, by means of a sensor identification transmitted from the sensor to the evaluation circuit. The computer program includes, moreover, at least one sensor type specific module corresponding to that of the sensor identification. In the following, this will also be referred to as the sensor type specific, computer program module, wherein the general module of the computer program is embodied, based on the detected sensor type, to load the specific module provided for this sensor type into a memory range provided therefor in the memory associated with the computer system, so that it can be executed by the computer system.

The evaluation circuit can have a first supplemental memory, for example, one embodied in the form of an SPI flash memory, in which are persistently stored such sensor type specific, computer program modules for a plurality of different sensor types connectable with the evaluation circuit, wherein the computer system is embodied, based on the sensor identification obtained from the sensor connected with the evaluation circuit, to install from the first supplemental memory into the memory associated with the computing unit a sensor type specific, computer program module associated with the sensor type. This permits plug and play operation of the measuring arrangement.

A further advantage of this embodiment is that the first supplemental memory can be embodied as bulk memory, which can provide a large number of different sensor type specific, computer program modules for the operation of a large number of different sensor types. Since these programs do not need to be held in the internal memory of the computer system, the computer system can be implemented by a relatively simple and price favorable microprocessor.

The evaluation circuit can have a second supplemental memory, especially an EEPROM, embodied for persistent storage of data. For example, the computer system can be embodied to store data in the second supplemental memory, especially diagnostic data or configuration data arising during operation.

An EEPROM serving as second supplemental memory can be embodied in such a manner that it is operable in an electrical current saving manner. This is especially advantageous when the third interface, via which the evaluation circuit is connected with the first superordinated data processing system, is a two-conductor interface. It is advantageous in this case to store data that can change during operation of the sensor, such as, for example, configuration data, counter states or calibration parameter, not in the internal flash memory associated with the computer system, but, instead, in the second supplemental memory, since the evaluation circuit and the sensor are supplied with energy only via the third interface embodied as a fieldbus interface, and, thus, only a limited power is available, which must be utilized simultaneously for the operation of the sensor, i.e. specially for registering the measured variable and its conversion into a measurement signal.

In an additional embodiment, which is advantageous especially for the case, in which the third interface, via which the evaluation circuit is connected with the first superordinated data processing system, is a two-conductor interface, the evaluation circuit can be embodied such that, while performing an updating of a computer program module stored in a memory of the evaluation circuit and/or of one or more, especially all, sensor type specific, computer program modules stored in a memory of the evaluation circuit, it takes into consideration the amount of power currently being provided to the evaluation circuit. Thus, for example, charging processes and memory processes can be slowed or, during a certain time period, deactivated. Along with that, the evaluation circuit can be embodied such that, during an updating of computer program modules, it interrupts the registering of measurement signals and/or other processing of measurement signals and/or the transmission of further processed measurement signals to the first and/or second data processing system. Thus, the entire energy, respectively power, provided via the third interface of the evaluation circuit can be dedicated to the updating of the relevant computer program modules.

The evaluation circuit can supplementally or alternatively also be embodied, while performing an updating of a computer program module contained in the computer system and/or of one or more, especially all, sensor type specific, computer program modules stored in a memory of the evaluation circuit, to set an electrical current of the signal output via the third interface to the first superordinated data processing system to an electrical current level, which lies above a measurement range and/or signals a malfunction. This is likewise advantageous for the case, in which the third interface, via which the evaluation circuit is connected with the first superordinated data processing system, is a two-conductor interface. For the case, in which the interface has a 4-20 mA HART electrical current output, for example, an error current of greater than 20 mA, especially 20.5 mA, can be output via the interface. Therewith, an as high as possible power is provided for updating the relevant computer program modules.

The evaluation circuit can be embodied, in the case of updating one or more computer program modules, especially in the case of updating all computer program modules, to load completely into a memory of the evaluation circuit in a first step a current version of the one or more computer program module's to be updated and only after the current version or the current versions is/are completely loaded, in a second step, to overwrite computer program modules to be updated present in a memory of the evaluation circuit. This has the advantage that, in the case of a defective, especially incomplete, transmission of the computer program modules to be updated to the evaluation circuit, the already present computer program modules remain unaffected and, therewith, functionally able, so that the measuring arrangement can, temporarily, still be operated with the existing computer program modules. This permits a destruction free updating of computer program modules of the evaluation circuit.

For updating computer program modules, the corresponding current computer program modules can be transmitted to the evaluation circuit from the sensor or from a device compatible with the second interface of the evaluation circuit via the second interface, from the first superordinated data processing system via the third interface or per radio by means of the second superordinated data processing system.

The sensor can be, for example, a sensor for measuring the pH-value, the conductivity, the oxygen content, an ion concentration, the chlorine content, the ozone content, the turbidity or a solids content of a liquid.

BRIEF DESCRIPTION OF THE DRAWINGS

The invention will now be explained in greater detail based on the examples of embodiments illustrated in the drawing, the figures of which show as follows:

FIG. 2 is a schematic view of the sensor and the evaluation circuit of the measuring arrangement illustrated in FIG. 1;

FIG. 4 is a schematic view of the sensor and the evaluation circuit of the measuring arrangement illustrated in FIG. 3.

DETAILED DISCUSSION IN CONJUNCTION WITH THE DRAWINGS

Figure 1:
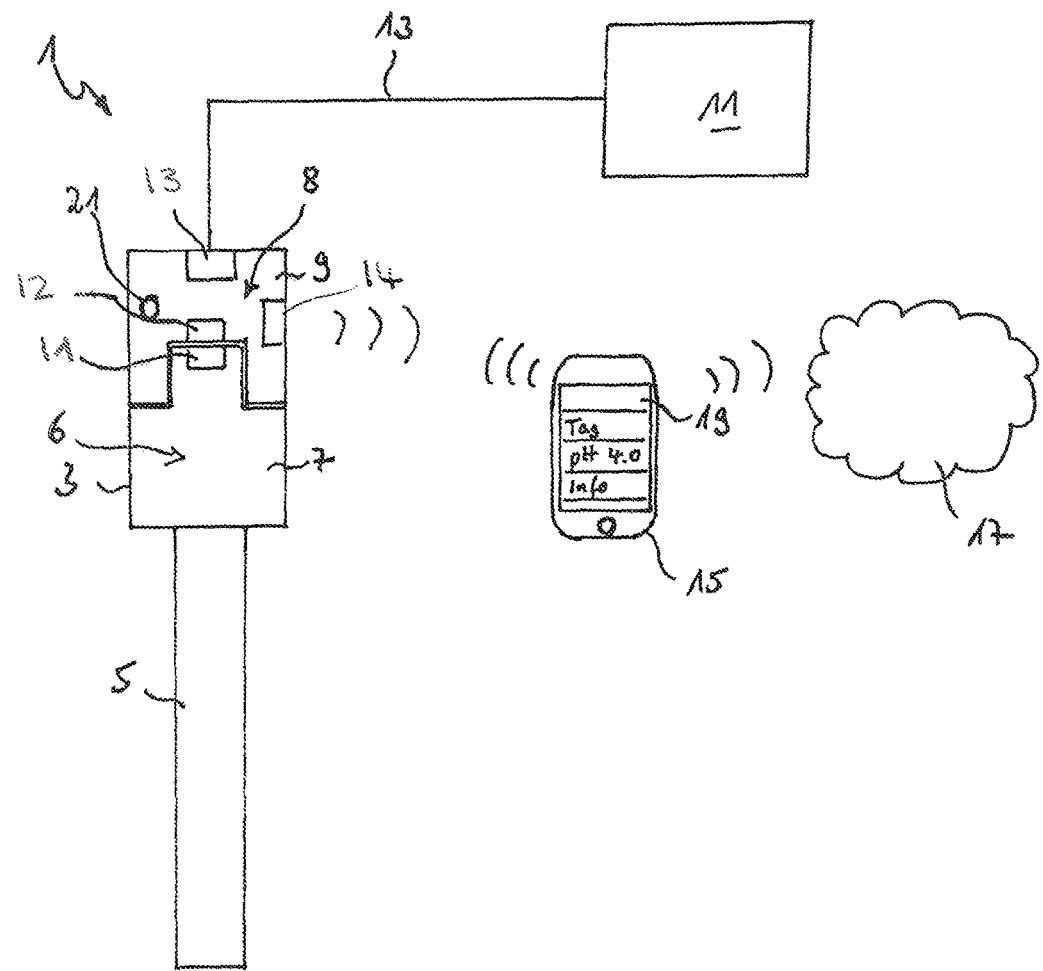
FIG. 1 is a schematic representation of a first example of an embodiment of a measuring arrangement having a sensor, an evaluation circuit, a superordinated first data processing system, and a second superordinated data processing system connected via radio with the evaluation circuit.

FIG. 1 shows schematically a measuring arrangement 1. Measuring arrangement 1 includes a sensor 3 having a measuring transducer 5 and a sensor side, primary coupling element 7 connected permanently with the measuring transducer 5. Primary coupling element 7 has a housing, in which a sensor circuit 6 is accommodated. Sensor circuit 6 includes especially a first interface I1, via which the sensor 3 can transmit a measurement signal to a second interface I2 belonging to an evaluation circuit 8 accommodated in the secondary coupling element 9. Second interface I2 is complementary to the first interface I1. The secondary coupling element 9 includes a second housing, which surrounds the evaluation circuit 8, especially liquid tightly, in order to protect evaluation circuit 8 against environmental influences. Also the housing of the sensor side coupling element 7 is liquid tightly sealed and so protects sensor circuit 6 against environmental influences. Evaluation circuit 8 is embodied as an electronic circuit, which can be arranged within the housing of the secondary coupling element 9 on an, especially, multi-ply circuit board, flexible circuit card or rigid-flex circuit card.

Evaluation circuit 8 is connected with a first superordinated data processing system 11, which can be, for example, a process control system, especially one comprising a PLC. The connection can be implemented, for example, by means of a fieldbus 13. Options, in such case, include both a wired connection as well as also a wireless connection. For transmission of data from the evaluation circuit 8 to the first superordinated data processing system 11 via the fieldbus 13, respectively for receiving data from the superordinated data processing system 11 by the evaluation circuit 8, such includes a fieldbus interface I3. Sensor 3, including the sensor circuit 6, as well as the evaluation circuit 8, are supplied with energy by the first superordinated data processing system 11 via the interface I3.

Data communication between the evaluation circuit 8 and the superordinated first data processing system 11 occurs by means of a communication protocol processable by the superordinated data processing system 11, for example, by means of a standard fieldbus communication protocol, such as HART, PROFIBUS PA, PROFIBUS DB, Foundation Fieldbus, ModBus. If the connection 13 is implemented as a wireless connection, the communication can occur, for example, according to the wireless HART standard. In the present example, interface I3 is embodied to enable communication of the evaluation circuit with the superordinated unit via a 4-20 mA HART signal and includes a two-conductor, electrical current output. Equally, the here described invention can, however, also be implemented with a measuring arrangement, in the case of which the evaluation circuit works with a four-conductor, electrical current output and in the case of which communication occurs by means of a 4-20 mA HART signal or by means of one of the other mentioned, standard, fieldbus communication protocols.

The pluggable connector coupling formed by the coupling elements 7 and 9 is embodied as an inductive coupling in the present example. Each of the coupling parts comprises a coil and energy and data can be inductively transmitted between these coils. This has the advantage that the pluggable connector coupling simultaneously assures galvanic isolation of the sensor 3 from the superordinated data processing system 11, respectively the evaluation circuit 8. Alternatively, the pluggable connector coupling can, however, also be embodied as a galvanic coupling, plugged connection. In this case, it is advantageous to provide galvanic isolation within the sensor circuit 6 or within the electronic circuit forming the evaluation circuit 8.

The secondary coupling element 9 includes an optical display 21, which can comprise e.g. an LED, for visual display of a state of the communication connection via the pluggable connector coupling established by the coupling elements 7, 9. The display can be embodied, for example, in the form of a multi-colored LED. In this case, each color corresponds to a certain state of the communication connection. In a variant, the optical display 21 can also serve to indicate sensor states, e.g. a sensor defect or other system states. It is also possible to use just a single color LED. In this case, mutually differing blink frequencies can serve for visualizing the system states or communication states.

Evaluation circuit 8 includes another interface I4, which in the present example is embodied as a radio interface. It includes a radio transceiver, which is embodied to communicate with a second superordinated data processing system 15 per radio, for example, according to a Bluetooth, or Bluetooth LE, standard. The second superordinated data processing system 15 is embodied in the present example as a smart phone. It includes besides a radio interface embodied for radio communication with the interface I4 of the evaluation circuit 8, for example, according to a Bluetooth, or Bluetooth LE, standard, an Internet interface, via which it can communicate, for example, per WLAN, GSM or UMTS, with a radio network 17, especially an intranet or the Internet.

The smart phone serving as second superordinated data processing system 15 includes a display and input means 19, which in the present example is embodied as a touch screen. Stored in a memory of the data processing system 15 is servicing software in the form of an app, which is executable by the data processing system 15. The servicing software is embodied to provide an HMI, which by means of one or more menus displays measuring and sensor data and/or measuring point parameters and provides a user the opportunity for inputting or selecting parameters and for input or selection of commands to the evaluation circuit.

FIG. 2 shows schematically the two coupling elements 7 and 9 with the therein arranged circuit components of the sensor circuit 6 and of the evaluation circuit 8. Sensor circuit 6 includes an analog measuring circuit MC, which in interaction with the measuring transducer 5 produces an analog measurement signal in the form of a measurement voltage or measurement current. The measurement signal is digitized by the analog/digital converter A/D1 and output to a first microprocessor μC1, which is embodied to prepare the measurement signal for transmission via the interface I1 to the interface I2 of the evaluation circuit 8. The first microprocessor μC1 includes an internal memory. Moreover, the sensor circuit 6 can comprise at least one additional supplemental memory (not shown), which the first microprocessor μC1 can access. Contained in this memory can be especially sensor-specific parameters, e.g. present calibration parameters, e.g. the parameters, zero point and slope, characterizing a sensor characteristic curve, as well as counter states. Evaluation circuit 8 includes a second microprocessor μC2 , which is embodied, among others things, to calculate from the measurement signal a measured value of the measured variable.

Microprocessor μC2 includes an internal flash memory F1 and an internal RAM R. Moreover, it can access a first supplemental memory SPI, which is embodied as bulk memory. It can, moreover, access a second supplemental memory F2 , in which durably stored, configuration data or other sensor or measuring point referenced data, which can change during operation of the sensor 3, are stored. Microprocessor μC2 is, moreover, connected with the interface I3 to the superordinated data processing system 11 and with the interface I4, which serves for radio communication with the second superordinated data processing system 15.

This measuring arrangement permits a plug and play operation:

Stored in the internal memory F1 of the second microprocessor μC2 is a first, general, computer program module, which is embodied to ascertain, based on an identification obtained from the sensor 3, the sensor type of the sensor 3. Contained in the first supplemental memory SPI are a large number of sensor type specific, program modules each associated with a particular sensor type and serving for determining a measured value from a measurement signal of the corresponding sensor type and/or for providing diagnostic functionalities for sensors of the associated sensor type or additional operating functions for the corresponding sensor type. The first computer program module is embodied to load, based on the ascertained sensor type, at least one further program module associated with the sensor type from the second supplemental memory SPI into the memory range of the internal memory F1 provided therefor.

Upon start-up of a new sensor, thus, based on the identification of the sensor type provided by the sensor, the specific computer program module required for operating the sensor can be loaded and executed by means of the evaluation circuit 8.

For maintenance of the sensor 3, such can be released from the evaluation circuit 8 by separating the plugged connection and subjected at another site, e.g. in a laboratory, to maintenance and/or calibration. A sensor of the same sensor type connected during this time with the evaluation circuit 8 can be put in operation immediately by means of the evaluation circuit 8 without other parametering or other measures. In the calibrating in the laboratory, the currently ascertained calibration data, especially zero point and slope of a (linear) sensor characteristic curve can be stored in a memory of the first microprocessor μC1 of the sensor circuit 6 or in a supplemental memory (not shown), which can be accessed by the first microprocessor μC1 of the sensor circuit 6. Upon connection of the sensor 3 to the evaluation circuit by means of the plugged connection, the second microprocessor μC2 can via the second interface load the current calibration data and store such in the second supplemental memory F2, so that it is available for calculating measured values from the measurement signals of the sensor 3. Also, other sensor data, especially diagnosis relevant data, can, in this way, be provided from the sensor circuit 6 to the evaluation circuit 8.

A calibrating of the sensor 3 can also be performed on-site by means of the second superordinated data processing system 15, without having to separate the sensor 3 from the evaluation circuit 8.

A updating of computer program modules stored in one of the memories F2 , SPI of the evaluation circuit 8 or a parametering and/or configuring can basically occur via the second interface I2, the third interface I3 or the radio interface I4. In the first case, a sensor 3 newly to be connected to the second interface can have in a memory of the sensor circuit current computer program modules or parameters, which after connection of the plugged connection can be transmitted from the sensor circuit via the first and second interfaces I1, I2 to the evaluation circuit 8. Alternatively, it is also an option to connect at the second interface I2 of the evaluation circuit a service device, which has an interface compatible with the second interface. Thus, the interface of the service device can be embodied identically to the first interface I1 of the sensor 3. The service device can have a computer system and a memory, which the computer system can access, and in which current computer program modules or parameters are stored. These can, after establishing the connection between the service device and the evaluation circuit 8, be transmitted to the evaluation circuit 8 and installed in a memory of the evaluation circuit 8.

Evaluation circuit 8 is embodied to interrupt the measurement operation of the measuring arrangement 1 in the case of an updating of all computer program modules present in the memories SPI, F1 of the evaluation circuit 8, which corresponds to a firmware update, or in the case of an updating of individual computer program modules. Then, the entire energy, respectively power, provided to the evaluation circuit via the third interface I3 is available for updating the relevant computer program modules.

Additionally, the evaluation circuit 8 is embodied to set, during the updating, the electrical current signal output via the two-conductor, electrical current output of the interface I3 to an error current of greater than 20 mA. Therewith, an as high as possible power is available for updating the relevant computer program modules.

Figure 3:
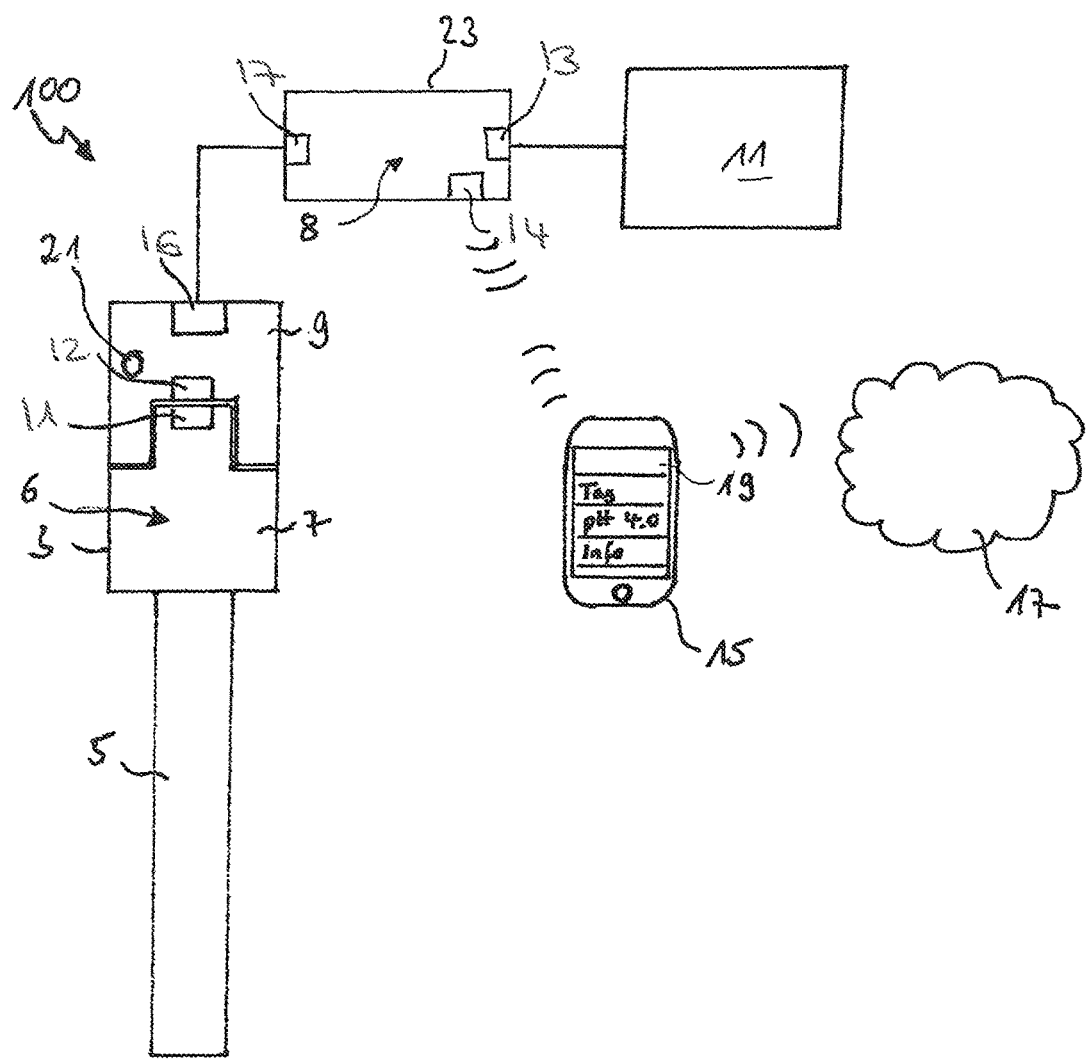
FIG. 3 is a schematic representation of a second example of an embodiment of a measuring arrangement having a sensor, an evaluation circuit, a superordinated first data processing system, and a second superordinated data processing system connected via radio with the evaluation circuit.

FIG. 3 shows, as a further example of an embodiment, a measuring arrangement 100, which includes a sensor 3, a coupling element 9 releasably connected with the sensor 3 and a compact transmitter 23 comprising an evaluation circuit 8, which is connected with a first superordinated data processing system 11, which is here embodied as a control system, and by means of a radio connection also with a second superordinated data processing system 15, here embodied as a smart phone. Features of the measuring arrangement 100, which are embodied identically to corresponding features of the measuring arrangement 1 of the first example of an embodiment illustrated in FIGS. 1 and 2, are provided with identical reference characters.

Sensor 3 includes a measuring transducer 5 as well as, contained in the primary side coupling element 7, a sensor circuit 6, which includes a first interface I1. The secondary coupling element 9 includes a circuit, which has a second interface I2 complementary to the first interface I1 and another interface I6. The circuit is especially embodied to receive signals from the sensor 3 via the interface I2, in given cases, to condition them and forward them via the interface I6 to the compact transmitter 23 as well as to receive signals obtained via the interface I6 from the compact transmitter 23, in given cases, to condition them and to forward them via the interface I2 to the sensor circuit 6. The interfaces I1 and I2 are, such as in the example of an embodiment in FIG. 1, embodied as inductive interfaces and the coupling elements 7 and 9 are embodied as releasably plugged connections.

The connection between the interface I6 of the coupling element 9 and the complementary interface I7 of the compact transmitter 23 is embodied in the example shown here as a solid cable connection. The compact transmitter 23 includes a housing, which in the present example is embodied as a hollow cylinder with an outer diameter of greater than 10 mm and less than 20 mm. The housing can be produced, for example, as an injection molded part of synthetic material, e.g. a plastic. The compact transmitter 23 has neither a display nor input means. Arranged in the housing of the compact transmitter 23 is the evaluation circuit 8, which serves especially for determining a measured value from a measurement signal transmitted from the sensor 3 via the plugged connection, as well as, in given cases, for additional processing of the measurement signal and for forwarding the measurement signal, respectively the further processed measurement signal, to the first superordinated data processing system 11 and/or to the second superordinated data processing system 15. Evaluation circuit 8 corresponds in construction and function to the evaluation circuit 8 described based on the first example of an embodiment presented in FIGS. 1 and 2. Evaluation circuit 8 is connected via a fieldbus 13 with the first superordinated data processing system 11 and via a radio connection with the second superordinated data processing system 15.

An advantage of this embodiment compared with the example of an embodiment illustrated in FIG. 1 is that the evaluation circuit 8 is accommodated in the compact transmitter 23 instead of in the secondary coupling element 9. This permits the housing of the coupling element 9 to be embodied relatively small, so that the sensor 3 with the pluggable connector coupling comprising the primary and secondary coupling elements 7, 9 can be accommodated in more conventional assemblies. In spite of this, the total structure remains, as a whole, compact, due to the small housing dimensions of the compact transmitter 23.

FIG. 4 shows schematically the primary coupling element 7, the secondary coupling element 9 and the cable transmitter 23. The primary coupling element 7 is connected durably with the measuring transducer 5 and contains the sensor circuit 6, which is embodied in construction and function identically to the sensor circuit 6 of the first example of an embodiment presented in FIGS. 1 and 2. The secondary coupling element 9 includes a microprocessor µC3, which is connected with the sensor side interface I2 and the cable transmitter side interface I6. The cable transmitter 23 includes the evaluation circuit 8, which, such as already mentioned, is essentially embodied identically to the evaluation circuit 8 of the first example of an embodiment. Evaluation circuit 8 includes here, however, a sensor-side interface I7, which is connected with the interface I6 of the secondary coupling element 9 for transmission of energy and data. Evaluation circuit 8 includes, moreover, a radio interface I4, via which the evaluation circuit 8 can communicate with the second superordinated data processing system 15 embodied as a smart phone. Along with that, the evaluation circuit 8 includes an interface I3 in the form of a fieldbus interface to the first superordinated data processing system 11. In the present example, interface I3 is embodied to enable communication of the evaluation circuit with the superordinated unit via a 4-20 mA HART signal and includes a two-conductor, electrical current output. Sensor 3, coupling element 9 and compact transmitter 23 are supplied with energy via the interface I3.

The measurement operation, as well as the updating of computer program modules and parameters or other data stored in the memories F1, F2, SPI of the evaluation circuit 8 occurs in equal manner to that described based on the example of an embodiment illustrated in FIGS. 1 and 2. Also in the present example, a plug and play operation is provided, in that a sensor 3 is connected to the secondary coupling element, and, via the interface I1, the secondary coupling element 9 and the sensor-side interface I7 of the evaluation circuit 8, an identification is transmitted. Based on the identification, a sensor-specific computer program module associated with the sensor type of the sensor 3 is loaded from the supplemental memory SPI into the internal memory F1 of the microprocessor µC2 and executed by such, in order to operate the sensor 3. Also, the managing of the energy provided via the fieldbus interface I3 during the updating of computer program modules can occur in the same manner as described based on the first example of an embodiment illustrated in FIGS. 1 and 2.

The invention claimed is:

1. A measuring arrangement, comprising:
   a sensor including a first interface, wherein the sensor is embodied to produce a measurement signal correlated with a measured variable and to output the measurement signal via the first interface;
   an evaluation circuit including:
      a second interface complementary to the first interface, wherein the second interface is releasably connected with the first interface;
      a third interface embodied to transmit and receive data and to receive electrical energy, wherein the evaluation circuit is embodied to receive operating energy via the third interface;
      a radio interface;
      a computer system having a memory;
      a computer program executable by the computer system, wherein the computer program is configured to process the measurement signal and to calculate a measured value based on the measurement signal; and
      a first supplemental memory in which are persistently stored sensor type specific computer program modules for a plurality of different sensor types connectable with the evaluation circuit;
   a first superordinated data processing system connected with the evaluation circuit via the third interface; and
   a second superordinated data processing system connected with the evaluation circuit wirelessly via the radio interface,
   wherein the computer program is further configured to obtain a sensor identification from the sensor and to install from the first supplemental memory into the computer system memory a sensor type specific computer program module based on the sensor identification, wherein the computer program is further configured to calculate, via the sensor type specific computer program module, a measured value based on the measurement signal, to convert the calculated measured value into a first signal according to a communication protocol processable by the first data processing system, to convert the calculated measured value into a second signal according to a communication protocol processable by the second data processing system, to forward the first signal to the first data processing system, and to forward the second signal to the second data processing system.

2. The measuring arrangement as claimed in claim 1, wherein:
said sensor and said evaluation circuit are connected with one another by means of a releasably plugged connection for transmission of data and energy.

3. The measuring arrangement as claimed in claim 2, wherein:
said plugged connection includes a sensor side, primary coupling element and a complementary, evaluation circuit side, secondary coupling element; and
said secondary coupling element has a housing, in which the evaluation circuit is arranged.

4. The measuring arrangement as claimed in claim 3, wherein:
said housing of said secondary coupling element protects the evaluation circuit from environmental influences by liquid tight sealing of the evaluation circuit.

5. The measuring arrangement as claimed in claim 3, wherein:
said housing of said secondary coupling element is embodied at least sectionally as a hollow cylinder with an outer diameter of less than 20 mm.

6. The measuring arrangement as claimed in claim 3, wherein:
said secondary and/or said primary coupling element includes a display element including an LED, for displaying a communication state and/or a system state.

7. The measuring arrangement as claimed in claim 1, wherein:
said second superordinated data processing system communicates via the radio connection with the evaluation circuit according to one of: a Bluetooth standard, according to the Bluetooth low energy protocol, or via wireless HART.

8. The measuring arrangement as claimed in claim 1, wherein:
said third interface is embodied to transmit data, including further processed measured values, from said evaluation circuit to said first superordinated data processing system via a fieldbus in the form of a signal according to a protocol meeting one of the following standards: HART, PROFIBUS PA, PROFIBUS DB, Foundation Fieldbus, and ModBus.

9. The measuring arrangement as claimed in claim 1, wherein:
said second data processing system is one of: a handheld, a smart phone, a tablet PC, a notebook or a display system embodied for wireless communication with the evaluation circuit.

10. The measuring arrangement as claimed in claim 1, wherein:
said second data processing system is a handheld adapted for use in an Ex-region or a display system adapted for use in an Ex-region and embodied for wireless communication with the evaluation circuit.

11. The measuring arrangement as claimed in claim 1, wherein:
said evaluation circuit is embodied to transmit current configuration parameter and/or menu structure data to said second superordinated data processing system.

12. The measuring arrangement as claimed in claim 1, wherein:
said second superordinated data processing system is embodied to transmit user predetermined configuration parameters to the evaluation circuit.

13. The measuring arrangement as claimed in claim 1, wherein:
said second data processing system has a WLAN, GSM, or UMTS communication interface to a radio network.

14. The measuring arrangement as claimed in claim 1, wherein:
said evaluation circuit has a second supplemental memory embodied for persistent storage of data, and said computer system is further configured to store data in the second supplemental memory, including diagnostic data or configuration data arising during operation.

15. The measuring arrangement as claimed in claim 1, wherein:
said evaluation circuit is embodied, while performing an updating of a computer program module stored in a memory of said evaluation circuit and/or of one or more sensor type specific, computer program modules stored in a memory of the evaluation circuit, to take into consideration the amount of power currently being provided to the evaluation circuit.

16. The measuring arrangement as claimed in claim 1, wherein:
said evaluation circuit is embodied, while performing an updating of a computer program module contained in a memory of the evaluation circuit and/or of one or more sensor type specific, computer program modules stored in a memory of said evaluation circuit, to set an electrical current of the signal output via said third interface to said first superordinated data processing system to an electrical current level, which lies above a measurement region and/or signals a malfunction.

17. The measuring arrangement as claimed in claim 1, wherein:
said evaluation circuit is embodied to load completely into a memory of said evaluation circuit in a first step a current version of one or more computer program modules to be updated and only after the current version or the current versions is/are completely loaded, in a second step, to overwrite computer program modules to be updated present in a memory of the evaluation circuit.

18. The measuring arrangement as claimed in claim 1, wherein the third interface includes a two-wire, 4-20 mA interface.

19. A method of start-up for a measuring arrangement, comprising:
providing a measuring arrangement, comprising:
a sensor including a first interface, wherein the sensor is embodied to produce a measurement signal correlated with a measured variable and to output the measurement signal via the first interface;
an evaluation circuit including:

a second interface complementary to the first interface, wherein the second interface is releasably connectable with the first interface;
a third interface embodied to transmit and receive data and to receive electrical energy, where in the evaluation circuit is embodied to receive operating energy via the third interface;
a radio interface;
a computer system having a memory;
a computer program executable by the computer system, wherein the computer program is configured to process the measurement signal and to calculate a measured value based on the measurement signal; and
a first supplemental memory in which are persistently stored sensor type specific computer program modules for a plurality of different sensor types connectable with the evaluation circuit;
a first superordinated data processing system connectable with the evaluation circuit via the third interface; and
a second superordinated data processing system connectable with the evaluation circuit wirelessly via the radio interface,
wherein the computer program is further configured to obtain a sensor identification from the sensor and to install from the first supplemental memory into the computer system memory a sensor type specific computer program module based on the sensor identification,
wherein the computer program is further configured to calculate, via the sensor type specific computer program module, a measured value based on the measurement signal, to convert the calculated measured value into a first signal according to a communication protocol processable by the first data processing system, to convert the calculated measured value into a second signal according to a communication protocol processable by the second data processing system, to forward the first signal to the first data processing system, and to forward the second signal to the second data processing system;
connecting the first interface of the sensor to the second, complementary interface of the evaluation circuit;
connecting the third interface of the evaluation circuit to the first superordinated data processing system;
providing energy from the first superordinated data processing system to the evaluation circuit and the sensor;
transmitting from the sensor to the evaluation circuit via the first interface and the second interface an identification of the sensor;
the computer program receiving the sensor identification and installing from the first supplemental memory into the computer system memory a sensor type specific computer program module based on the sensor identification;
the computer program operating the sensor to obtain the measurement signal via the first interface and the second interface; and
the computer program calculating via the sensor type specific computer program module the measured value based on the measurement signal.

* * * * *